United States Patent
Pauser (10) Patent No.: US 8,602,775 B2
(45) Date of Patent: Dec. 10, 2013

(54) DEVICE FOR DISPENSING A DENTAL COMPOSITION

(75) Inventor: Helmut Pauser, Diessen (DE)

(73) Assignee: 3M Innovative Properties Company, Saint Paul, MN (US)

( * ) Notice: Subject to any disclaimer, the term of this patent is extended or adjusted under 35 U.S.C. 154(b) by 67 days.

(21) Appl. No.: 12/993,918

(22) PCT Filed: Apr. 24, 2009

(86) PCT No.: PCT/US2009/041657
§ 371 (c)(1),
(2), (4) Date: Feb. 11, 2011

(87) PCT Pub. No.: WO2009/154871
PCT Pub. Date: Dec. 23, 2009

(65) Prior Publication Data
US 2011/0129794 A1    Jun. 2, 2011

(30) Foreign Application Priority Data

May 28, 2008    (GB) .................................. 0809545.7

(51) Int. Cl.
*A61C 5/04*    (2006.01)

(52) U.S. Cl.
USPC .......................................................... 433/90

(58) Field of Classification Search
USPC ........ 433/80, 89, 90; 222/325–327, 336, 339, 222/340, 386, 391; 604/57–61, 63, 121, 604/124, 125, 135, 181, 187, 208–211, 220, 604/223, 228, 232, 234; 128/DIG. 12; 206/570, 572, 368; 267/155, 157, 174; 74/592
See application file for complete search history.

(56) References Cited

U.S. PATENT DOCUMENTS

| | | | |
|---|---|---|---|
| 2,070,206 A | | 2/1937 | Hudson |
| 3,381,861 A | | 5/1968 | Stein |
| 4,472,141 A | | 9/1984 | Dragan |
| 4,993,948 A | | 2/1991 | Cameron et al. |
| 5,125,836 A | | 6/1992 | Dragan et al. |
| 5,263,614 A | * | 11/1993 | Jacobsen et al. ............... 222/137 |
| 5,871,354 A | * | 2/1999 | Kunkel et al. ................... 433/89 |
| 6,254,389 B1 | | 7/2001 | Seghatol |
| 6,312,254 B1 | | 11/2001 | Friedman |
| 6,945,436 B2 | | 9/2005 | Mayer |
| 2004/0126733 A1 | | 7/2004 | Ronvig |
| 2006/0106342 A1 | * | 5/2006 | Cox .............................. 604/110 |

FOREIGN PATENT DOCUMENTS

| | | |
|---|---|---|
| WO | WO 97/21394 | 6/1997 |
| WO | WO 03/061508 | 7/2003 |

OTHER PUBLICATIONS

International Search Report for International Application No. PCT/US2009/041657, dated Nov. 25, 2009.

* cited by examiner

*Primary Examiner* — Heidi M Eide
*Assistant Examiner* — Justin O'Donnell
(74) *Attorney, Agent, or Firm* — Qiang Han; 3M Innovative Properties Company (57) ABSTRACT

A device for dispensing a dental composition is provided. The device has a plunger for extruding dental composition from a container, an energy accumulator for advancing the plunger, and an actuator for charging the energy accumulator. The force for actuating the actuator is lower than the force at which the plunger can be advanced. The device preferably provides convenient dispensation of dental compositions.

14 Claims, 5 Drawing Sheets

DEVICE FOR DISPENSING A DENTAL COMPOSITION

CROSS REFERENCE TO RELATED APPLICATIONS

This application is a national stage filing under 35 U.S.C. 371 of PCT/US2009/041657, filed Apr. 24, 2009, which claims priority to Great Britain Patent Application No. 0809545.7, filed May. 28, 2008, the disclosure of which are incorporated by reference in their entirety herein.

FIELD OF THE INVENTION

The invention relates to a device and method for dispensing a dental composition.

BACKGROUND OF THE INVENTION

In dentistry a number of dental compositions are provided in containers like cartridges, capsules and syringes. Often such containers are made for single use and are pre-filled with a dental composition. A variety of containers are available which can be used with a re-usable applicator. Therefore a system for dispensing the dental composition often includes an applicator and a container that can be inserted into and removed from a receptacle of the applicator. Applicators available on the market typically include a plunger that is adapted to extrude dental composition from the container.

For example WO 97/21394 discloses a dispensing applicator including a body with a handle, a pivotable lever and a front holder with a receptacle that is adapted to receive a dual chamber cartridge.

U.S. Pat. No. 5,125,836 discloses a manual extruder for receiving a cartridge at a front end. The extruder includes a pivoting handle attached to a finger grip handle. A plunger arranged in the extruder can be advanced by the pivoting handle. When the pivoting handle is squeezed closer to the finger grip handle, the plunger is moved toward the front end of the extruder. The plunger thus can be moved into the cartridge for extruding material from the cartridge.

Another applicator for dispensing dental compositions is disclosed in WO 03/061508. The applicator comprises a syringe body in which a specific amount of the composition is stored. The composition is dispensed from the syringe body to the desired location via a hollow dispensing needle by a displacing piston. The displacing piston is actuated by a force device arranged in a spring motor part of the applicator. The flow path between the inside of the syringe body and the dispensing hollow needle is controlled by a valve which is connected to a manual actuating unit positioned at the syringe body.

Finally, U.S. Pat. No. 4,993,948 discloses a cylinder containing tooth-filling material for hands-free use by a dentist. The filling material can be urged out of the cylinder by spring pressure. The flow of the material out of the cylinder through a nozzle is under the control of a valve located so that it can be readily manipulated between open and closed positions by the same hand of the dentist that controls the valve. The filling material is in a discrete capsule containing enough filling material for several teeth, and it may be easily placed into and removed from the cylinder.

It is still desirable to provide a dispensing device which is convenient to use with different dental compositions and different types of containers available on the market. Further there is still a need for a dispensing device which can be manufactured at relatively low cost, and which fulfils requirements particularly related to the dental field.

SUMMARY OF THE INVENTION

A first aspect of the invention relates to a device for dispensing a dental composition. The device comprises a plunger for extruding the dental composition from a container, an energy accumulator connectable to the plunger to advance the plunger at an extrusion force, and an actuator which can be actuated for charging the energy accumulator. The device further comprises a force converter which allows the actuator to be actuated at an actuation force that is lower than the extrusion force available from the energy accumulator to advance the plunger.

The invention may be advantageous for dispensing a dental composition in a precise position, and particularly for continuously dispensing a dental composition along a path where accuracy is desirable. The dispensing device allows for separating the actuation of the device and the dispensation of the dental composition from the container. Therefore actuations that may cause a user to agitate the overall device may be avoided during dispensation of the composition using the present invention. The dispensing device may also allow for accumulating energy from actuations of the device which then may be used to extrude the dental composition. Therefore the device preferably allows extrusion of a dental composition at relatively high forces, but preferably enables actuation at relatively low forces. Thus the device may be generally convenient to use.

The extrusion force provided by the energy accumulator may be a potential extrusion force. Therefore the extrusion force may correspond to a force that is generally available for advancing the plunger, or for extruding the dental composition from the container. However, the actual extrusion force used for extruding the dental composition may also be lower, depending on characteristics of the container and/or the dental composition used.

In one embodiment of the device of the invention the actuator is adapted for manual actuation. The actuator may therefore comprise a handle which is shaped and sized to fit a user's hand for actuation. In a preferred embodiment the actuator comprises a lever that is pivotable for actuation. The actuator is preferably connected or connectable to the plunger of the device. An actuation may therefore cause the plunger to move. An actuation may comprise a working stroke and a return stroke. Preferably the working stroke causes the plunger to move, and the return stroke is independent from a movement of the plunger. In a preferred embodiment the working stroke causes the plunger to retract, for example to move in a direction away from the container. Preferably the connection between the actuator and the plunger comprises a force converter. Thus a user may actuate the actuator at relatively low forces that are converted into relatively high forces for moving the plunger, and thereby for charging the energy accumulator. This may also be advantageous in use of the device with high-viscosity dental compositions because the high relatively forces transmitted to the energy accumulator may later be used to extrude the dental composition.

In another embodiment the force converter may converts a first motion of the actuator into a second motion for charging the energy accumulator at a certain force conversion ratio between the first and second motions. The force conversion ratio between the first and second motions is preferably between about 3:1 and about 10:1, for example selected from among approximately 3:1, 7:1, 8:1 and 10:1. The extrusion force and the force used to charge the energy accumulator may generally correspond to each other in magnitude. Therefore the actuating force may be lower than the charging force and lower than the extrusion force. In particular the actuation force may be from approximately $\frac{1}{3}$ to $\frac{1}{10}$ of the extrusion force provided by (or available from) the device of the invention. For example, if the actuation force is about $\frac{1}{10}$ of the extrusion force, 10 working strokes at an actuation force of about 50 N would provide sufficient energy to extrude a certain composition requiring about a 500 N extrusion force. In certain embodiments the energy accumulator may require a minimum charging force, and as the energy accumulator is further charged the charging force increases. For example a mechanical spring used as energy accumulator may have such a spring characteristic. In this case the relationship between the actuation force and charging force may be proportional to one another, for example linearly, or progressively proportionally increasing, but still with the actuation force being lower than the charging force. Consequently also the extrusion force may change with extrusion progresses, for example according to the spring characteristic of a mechanical spring. For example the extrusion force may be higher at a beginning of an extrusion process and lower toward the end.

In still another embodiment the force converter may convert a third motion transferred from the energy accumulator into a fourth motion for advancing the plunger. In this case the force converter may be comprised in the connection between the energy accumulator and the plunger. The force conversion ratio between the third and fourth motions is preferably selected from among approximately 3:1, 7:1, 8:1, and 10:1. Thus a user may be able to actuate the actuator at an actuation force that is lower than the extrusion force.

Another embodiment may have a force converter in the connection between the actuator and another force converter in the connection between the energy accumulator and the plunger. This may allow for an even greater difference between the actuation force and the extrusion force.

In one embodiment the energy accumulator and the plunger cooperate such that energy from the energy accumulator is releasable for advancing the plunger. Further the energy accumulator and the plunger may cooperate so that a retraction of the plunger causes the energy accumulator to be charged. Actuations of the actuator may thus cause the energy accumulator to be charged. Therefore actuations of the actuator may supply energy to the energy accumulator with multiple actuations supplying fractional portions of energy being accumulated in the energy accumulator. Thus, portions of the accumulated energy that may be greater than the fractional portions may be made available to dispense the dental composition.

In another embodiment the dispensing device of the invention comprises a release mechanism. The release mechanism is preferably adapted to prevent advancement of the plunger (preferably with and without the presence of a container in the device). Therefore the plunger may be retracted whereby the energy accumulator is charged, and may be retained in the "charged" position. This may allow for incrementally charging the energy accumulator, for example by retracting the plunger stepwise due to multiple working strokes applied to the actuator. The release mechanism is preferably also adapted to permit advancement of the plunger. Therefore, once the energy accumulator is sufficiently charged the release mechanism may be actuated to permit the plunger to be advanced. Thus the release mechanism is preferably operable in a first and second mode of operation, with the first mode preventing the advancement of the plunger, and the second mode permitting the advancement of the plunger. Preferably the release mechanism is adapted to be switched on and off at any time. Therefore a user may first charge the energy accumulator, and afterwards stepwise dispense small amounts of dental composition to a desired location.

Preferably the release mechanism allows retraction of the plunger in the first and second operation modes. Therefore the plunger may be retracted at any time independent from the mode in which the release mechanism is switched. This allows a user to charge the energy accumulator while the release mechanism prevents advancement of the plunger in the opposite direction.

In a further embodiment the device of the invention comprises a one-way clutch that is movable by the actuator. The one-way clutch is preferably adapted to retract the plunger when moved in a first direction, but is movable relative to the plunger when moved in a second direction opposite the first direction. The one way-clutch may therefore be in engagement with the plunger and restrict relative movement between the clutch and the plunger in one direction, but allow relative movement in the opposite direction. However the one-way clutch may also be disengaged from the plunger. In this case the movement of the plunger in both directions is preferably selectively enabled. The actuator may, for example, drive the one-way clutch. The actuator therefore actuated in the working stroke may move the one-way clutch from an initial position towards the first direction. The one-way clutch thereby may engage and retract the plunger. And the actuator actuated in the return stroke or released to return may move the one-way clutch back into the initial position. In the initial position the one-way clutch preferably automatically disengages from the plunger so that an advancement of the plunger, for example caused by the energy accumulator, relative to the one-way clutch is enabled. A preferred embodiment of a one-way clutch comprises a so-called clamp plate mechanism as is described in more detail in the description of the figures.

In one embodiment the energy accumulator is adapted to accumulate mechanical energy.

A suitable energy accumulator may be a spring, for example a helical compression or tension spring. However any other mechanical spring types may be used as appropriate, as for example a leaf spring or spiral spring. In other embodiments a pneumatic cylinder or chamber may be used as so-called pneumatic springs. Pneumatic springs may provide for a relatively flat spring characteristic, for example a relatively flat linear spring response relative to mechanical springs. Other possible springs may comprise elastic materials, for example foamed rubber materials, which particularly may be relatively cheap and light weight.

In one embodiment the device of the invention is combined with a container. The container is preferably filled with the dental composition, and preferably has a plunger for extruding the dental composition from the container. In particular the plunger at least at its front side may be shaped to cooperate with the container containing the dental composition.

In one embodiment the container is a cartridge or capsule. Such a container preferably has a container body forming a chamber that is filled with or adapted to receive the dental composition. The chamber preferably opens at a front end into a nozzle for dispensation of the dental composition, and is closed by a piston at a rear end. The piston is preferably slidably arranged within the chamber, and is movable from the rear end towards the front end to extrude the dental composition from the container. The container preferably has an adaptor part which corresponds to a complementary adaptor part of the dispensing device. For example the container may have a raised rim adjacent a rear end which fits into a correspondingly sized and shaped recess in the device. Such an adaptor preferably allows the container to remain in a fixed position within the device.

The nozzle may have an outlet diameter which is adapted to provide a certain flow rate of the dental composition, which may depend on the viscosity of the dental composition and the extrusion force available at the device. Preferred outlet diameters are between 0.4 mm and 1 mm. Preferred forces are between 10 N and 2000 N, in particular between about 100 N and about 1200 N, and in more particular between about 500 N and 1000 N. The mentioned parameters may be particularly advantageous for a use of the device to provide a dental retraction composition.

A second aspect of the invention is directed to a method of dispensing a material. The method comprises the steps of:
actuating an actuator of a dispensing device at an actuation force; and
extruding the dental composition independently from actuating the actuator at an extrusion force; wherein the actuation force is lower than the extrusion force. The actuation force may for example be one of lower than about 75% of the extrusion force, lower than about 50% of the extrusion force, and lower than about 10% of the extrusion force.

The extrusion of the dental composition independent from actuating the device may provide for relative precise dispensation of the dental composition to a desired place, particularly along a continuous path, at least in part because it is not necessary to move the actuator of the device during dispensation of the composition.

A third aspect of the invention is related to a kit of parts. The kit preferably comprises a device according to the invention, and a plurality of springs having different spring characteristics. The springs are preferably exchangeable in the device. Therefore the device may be adjusted to provide different extrusion forces as required for use with different dental compositions, for example for dental compositions having different viscosities. This may allow for a user to adjust the flow rate at which the materials are dispensed from the device. The springs or the dental material cartridges or both may be marked to indicate the spring force that is required or preferred for common applications.

BRIEF DESCRIPTION OF THE DRAWINGS

The invention is described in the following with reference to the accompanying drawings, in which.

DETAILED DESCRIPTION OF THE INVENTION

Figure 1:
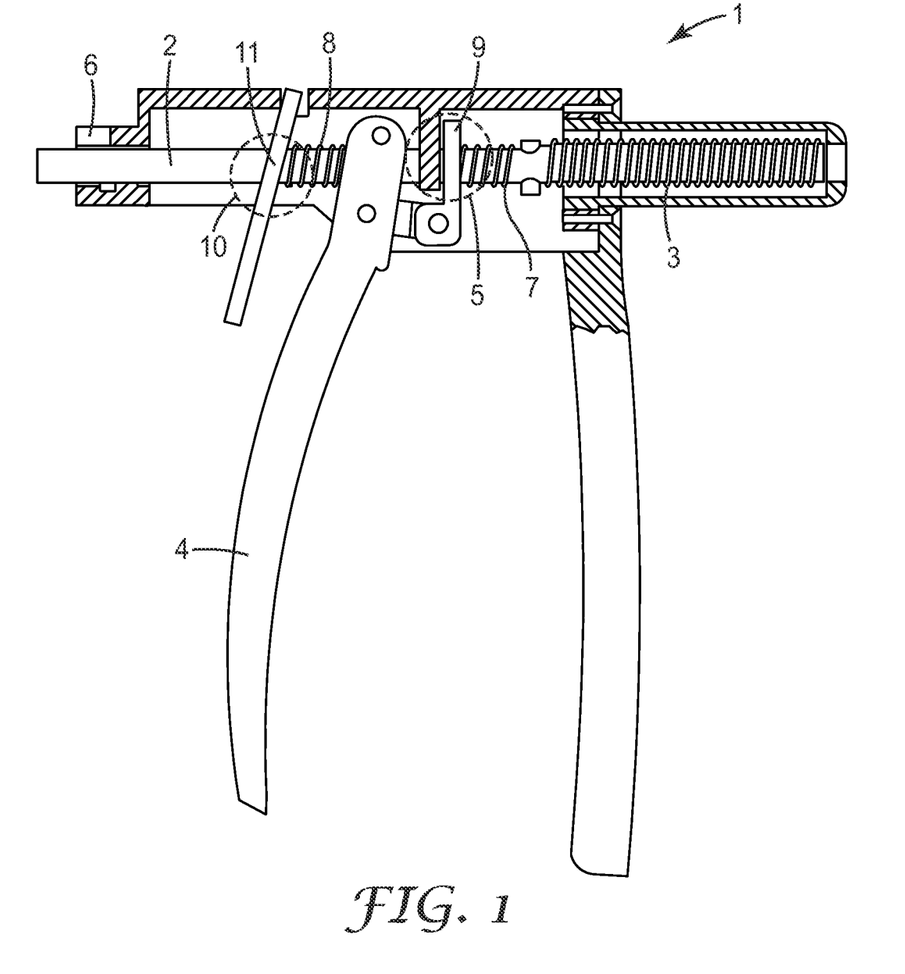
FIG. 1 is a cross-sectional view of a first embodiment of the device according to the invention in an initial state.

FIG. 1 shows a dispensing device 1 according to the invention. Although not shown in FIG. 1, the dispensing device 1 may be used to extrude a dental composition from a container such as a cartridge or a capsule. The dispensing device 1 comprises an actuator 4, a plunger 2, and a spring 3. The spring 3 forms an energy accumulator in the sense of the invention which is adapted to store energy in the form of a spring force. However other types of energy accumulators are possible which are adapted to accumulate mechanical energy, like differently shaped springs, a pneumatic spring, or any kind of resilient device which tends to return to its original size and/or shape after being compressed.

The dispensing device 1 may generally be used to dispense the dental composition by the use of energy from the energy accumulator. The energy accumulator may further be chargeable by actuating the actuator. Therefore the dispensating of the dental composition may be independent from the actuating of the actuator, unlike most conventional devices in which actuation and dispensation happen essentially simultaneously. For example, for dispensation of the dental composition to a desired location a user may use energy stored in the energy accumulator, without actuating the actuator. Because actuations may cause a user to agitate the device, the dispensing device may be guided relatively precisely and steadily, which can be an advantage of the present invention.

The dispensing device 1 has a mouthpiece 6 comprising an adaptor for receiving the container (not shown in FIG. 1). The plunger 2 is arranged in the dispensing device 1 so that it is movable within the container, for example to advance a piston of the container to extrude the composition. In the example shown in FIG. 1, the spring 3 is connected to or engages with the plunger 2 so that spring force can be made available to advance the plunger. On the other hand a retraction of the plunger 2 causes the spring 3 to be loaded. In this embodiment a compression spring is shown, however in other embodiments a tension or torsion spring may be used which may be loaded by tension rather than by compression. The plunger 2 is retractable by a first one-way clutch 5. The first one-way clutch 5 allows free movement of the clutch relative to the plunger in one direction, but locks the plunger against movement in the opposite direction. Therefore the first one-way clutch 5 moved from an initial position towards a first direction (in the Figure from left to right) and may engage and thereby retract the plunger 2, but may be reset in a second direction to the initial position (in the Figure from right to left) without moving the plunger 2 to any significant extent. In the initial position the one-way clutch 5 is disengaged from the plunger 2 so that the plunger 2 is freely movable relative to the one-way clutch 5. In the example the first one-way clutch 5 comprises a clamp plate 9 having a passage through which the plunger 2 extends. The clamp plate 9 with the passage aligned generally coaxially with the plunger is generally freely movable relative to the plunger, for example as shown in FIG. 1. However the clamp plate 9 may be inclined relative to the plunger 2 (indicated in FIG. 2) so that edges of walls that form the passage engage with the outer surface of the plunger 2, and thereby lock with the plunger 2. The clamp plate 9 is urged towards the initial position by a retaining spring 7 that is held in an orientation in which the clamp plate disengages the plunger 2. In this position of the clamp plate 9, the plunger 2 is freely moveable relative to the clamp plate 9 in the first and second directions.

The dispensing device 1 further has a release mechanism which comprises a second one-way clutch 10 which generally operates like the first one-way clutch 5, but engages the plunger 2 in an initial position. Thus in the initial position of the release mechanism the plunger 2 is locked against movement in the first direction, but is freely movable in the second direction. The second one-way clutch 10, like the first one-way clutch 5, comprises a clamp plate 11 locking the plunger 2 against any significant movement in one direction, but provides free movability of the plunger 2 relative to the clamp plate 11 in the opposite direction. A retaining spring 8 urges the clamp plate 11 towards the initial position in which the clamp plate 11 engages the plunger 2.

Figure 2:
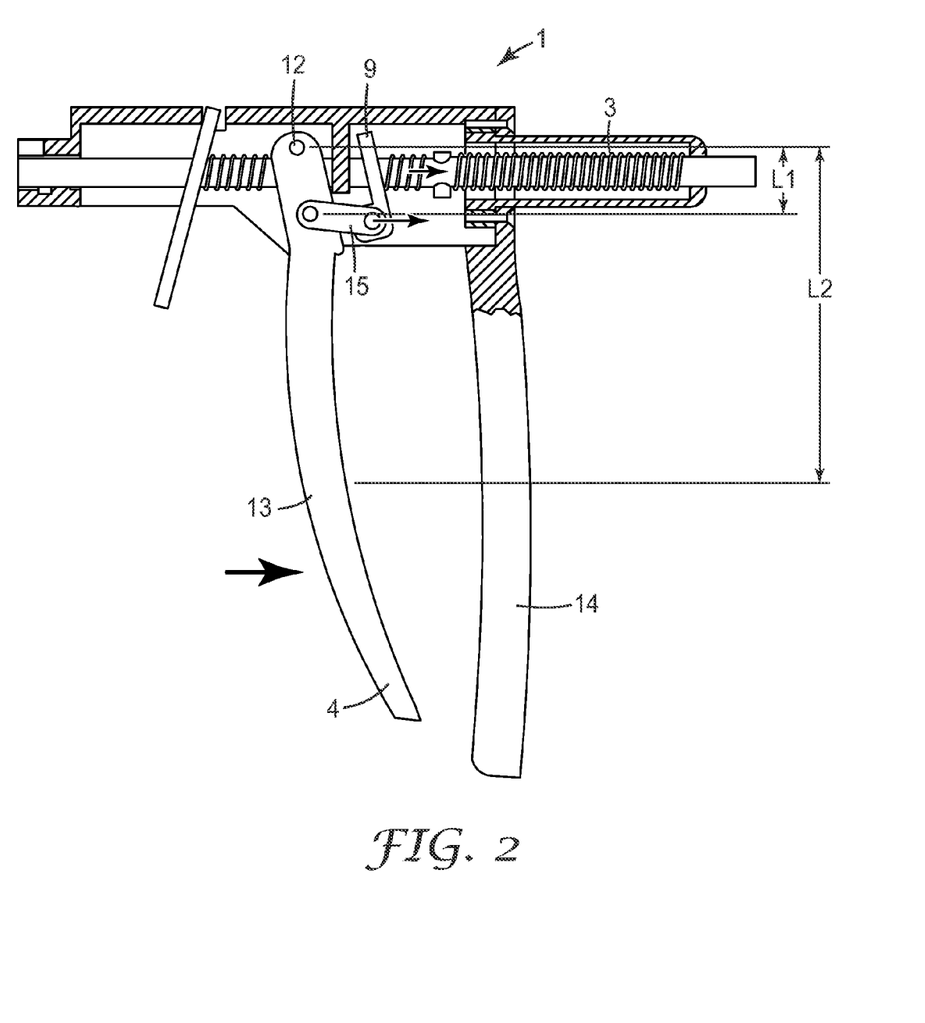
FIG. 2 shows the device of FIG. 1 in a partly loaded state.

In FIG. 2 the dispensing device 1 is shown while the actuator 4 is operated. The actuator 4 is pivotable around a hinge or pin 12, and comprises a first handle 13. The first handle 13 preferably allows a user to conveniently actuate the actuator 4. The dispensing device 1 is further preferably configured and dimensioned for one-handed operation. For example the dispensing device 1 may have a second handle 14 by which a user may hold or support the device. Preferably the actuator 4 in an initial position is placed with the handle 13 remote from the second handle 14 and in a working stroke is movable toward the second handle 14. During the working stroke the clamp plate 9 is moved in the second direction causing the plunger 2 to be retracted, and thereby loads the spring 3. The clamp plate 9 is driven by the actuator 4, in the example via a connecting rod 15. The connecting rod 15 is attached to the actuator at a distance L1 to the hinge 12. In contrast, the distance L2 approximately indicates the area a resulting actuation force is applied to by a user to the actuator 4. Because the distance L2 is greater than the distance L1, the actuator provides leverage which converts a motion of the handle 13 into a smaller motion of the clamp plate 9. In other words the dispensing device has a force converter converting the actuation force into a higher force for loading the spring 3. The force required to load the spring may generally correspond to the available extrusion force, because both forces depend on the characteristics of the same spring. Therefore the force converter generally converts a smaller actuation force into a larger extrusion force. Multiple working strokes may be used to sufficiently load the spring 3, and more than one spring or its equivalent may be provided. Thereby the energy of multiple strokes may be stored in the spring or energy accumulator(s), and made available for dispensing the dental composition later. The force conversion may be achieved by leverage as described, but a variety of other solutions are possible. For example, the actuator may act on the energy accumulator via a transmission, for example a gear reduction, a worm gear, a (gear) belt-drive, a hydraulic or pneumatic transmission, a chain drive, a friction gear transmission, and combinations thereof.

Figure 3:
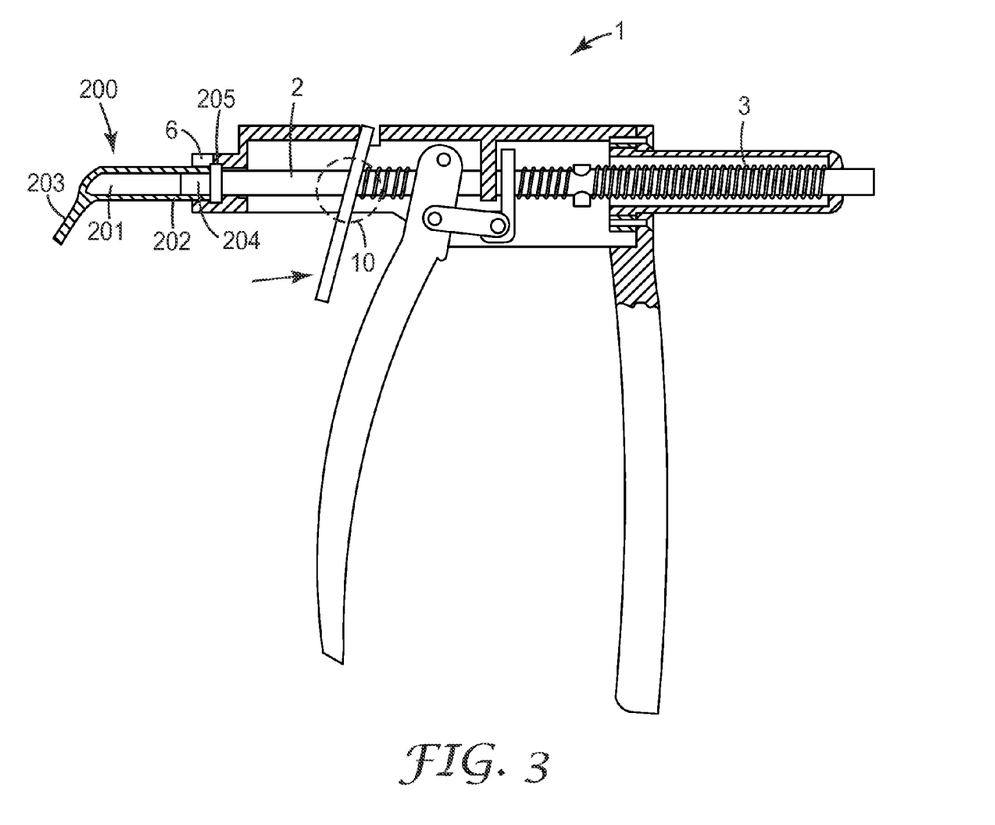
FIG. 3 shows the device of FIG. 1 in a loaded state.

FIG. 3 shows the dispensing device 1 in a substantially completely loaded state. The release mechanism in the initial position causes the second one-way clutch 10 to retain the plunger 2 that is now pre-loaded by the spring 3. However, the release mechanism may be actuated (as indicated by the arrow in the Figure) so that the second one-way clutch 10 disengages from the plunger 2. Thereby the plunger 2 is released and may be advanced from the spring force. The release mechanism may return toward or to the initial position (in a direction opposite the arrow in the Figure), and thus the plunger 2 stopped as desired. This allows the dispensation to be controlled (interrupted and/or continued) as desired by the user.

In use, a container 200 holding a flowable dental composition 201 is received in the mouthpiece 6 of the dispensing device 1. The dental composition 201 is, for example, selected from among a dental restorative material, a dental retraction material, a dental filling material, a dental luting or orthodontic cement, a dental impression material, a dental etching gel, a dental adhesive, and a dental sealant. Commercial examples of dental restorative materials include Z100 Restorative, Filtek Z250 Universal Restorative, and Filtek Supreme Universal Restorative, all available from 3M Company, St. Paul, Minn. In a preferred embodiment the dental composition is a dental retraction material, for example as available under the designation Expasyl™, form the company Produits Dentaires Pierre Rolland, France. Dental retraction material may be particularly advantageously used with the present invention because the dispensing device of the invention may provide the high application forces often required to extrude high-viscosity dental retraction materials. Further the device may be precisely and smoothly guided by a user, which is generally desirable for dispensing the material around a tooth in a patient's mouth.

The container 200 has a body portion 202 comprising a chamber in which the flowable composition 201 is contained. The chamber opens into a dispensing nozzle 203 at a front end, and is closed by a piston 204 at a rear end. The container further comprises a raised rim 205 for engagement with a recess in the mouth piece 6. The container may be closed by a cap or the equivalent at the front end, for example to prevent the composition from premature hardening. A device as it may be used with the present invention is available under the trade designation Aplicap, and Aplicap from 3M ESPE AG, Germany.

For discharging the dental composition 201 out of the container 200, the release mechanism may be actuated to unlock the plunger 2 which then is advanced due to the spring force. The plunger 2 is adapted to move into the container and to advance the piston 204 toward the nozzle. The dispensation of the dental composition 201 out of the container 200 may be interrupted at any time by releasing or resetting the release mechanism to the initial position. Thus, the energy loaded into the spring 3 can be released intermittently. The plunger may be retracted slightly to stop dispensation immediately.

Figure 4:
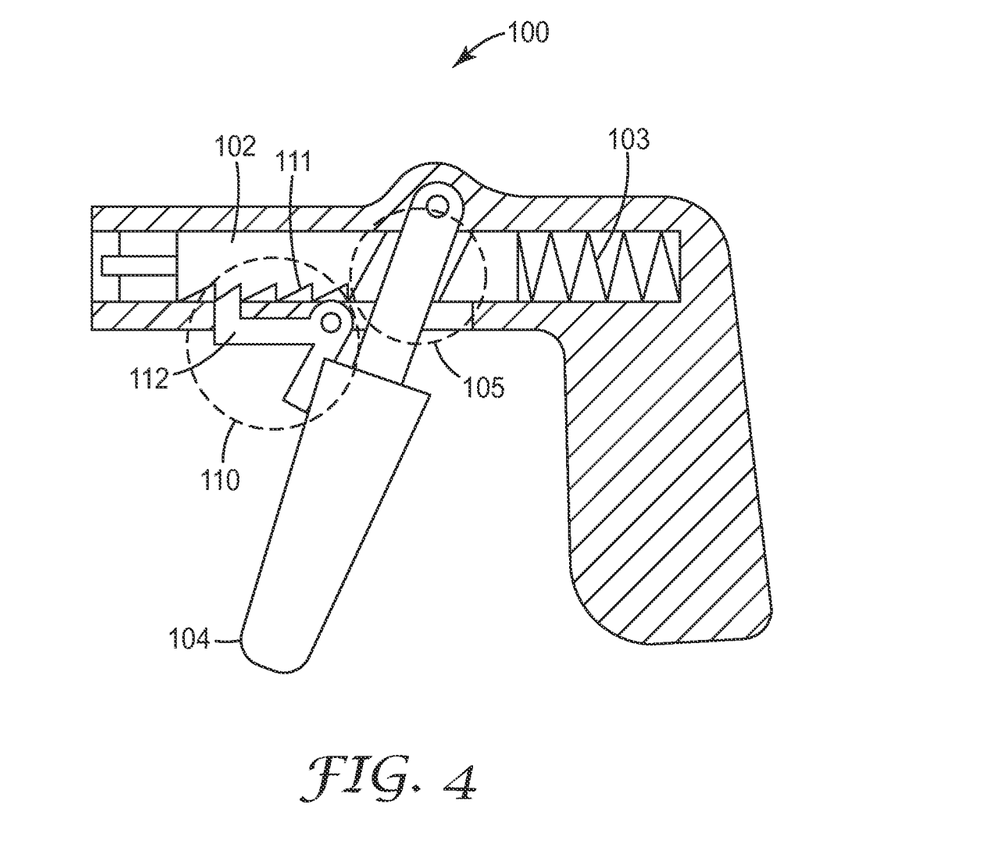
FIG. 4 shows a second embodiment of the device according to the invention in an unloaded state.

In FIG. 4 another embodiment of a dispensing device 100 is shown. The dispensing device 100 is generally configured like the device shown in FIGS. 1 to 3. However, the dispensing device 100 only has one clutch in a release mechanism 110. Therefore the device may be relatively inexpensive to manufacture. The dispensing device 100 has an actuator 104, a plunger 102 and a spring 103. In this example the actuator 104 and the plunger 102 are connected by a coupling 105. As shown, the actuator 104 is provided with a space between two end positions relative to the plunger 102. This allows the actuator 104 to be moved from an initial position toward a second direction (from left to the right in the Figure) so that the plunger 102 is retracted. Once the plunger 102 is retracted the space allows the actuator to be moved in the opposite direction relative to the plunger 102. Thus the actuator 104 may be reset to the initial position. However the space is optional, because resetting of the actuator 104 may not be necessary because in this embodiment a single working stroke is sufficient to load the spring 103. As explained above the device provides leverage between the area to which the actuation force is applied and the area of the actuator 104 that connects to the plunger 102. Thus this embodiment also comprises a force converter according to a feature of the invention.

The actuator when moved in the second direction retracts the plunger 102. Again the plunger 102 when retracted loads the spring 103. The plunger 102 has teeth 111 along at least a portion of its length which are adapted to be engaged by a ratchet 112 of the release mechanism 110. The ratchet 112 and the teeth 111 of the plunger 102 form the clutch that is used in the release mechanism 110. The teeth 111 are generally saw-shaped and oriented so that the ratchet locks with the teeth of the plunger 102 when the plunger 102 is urged in the first direction, but permit movement in the opposite direction.

Figure 5:
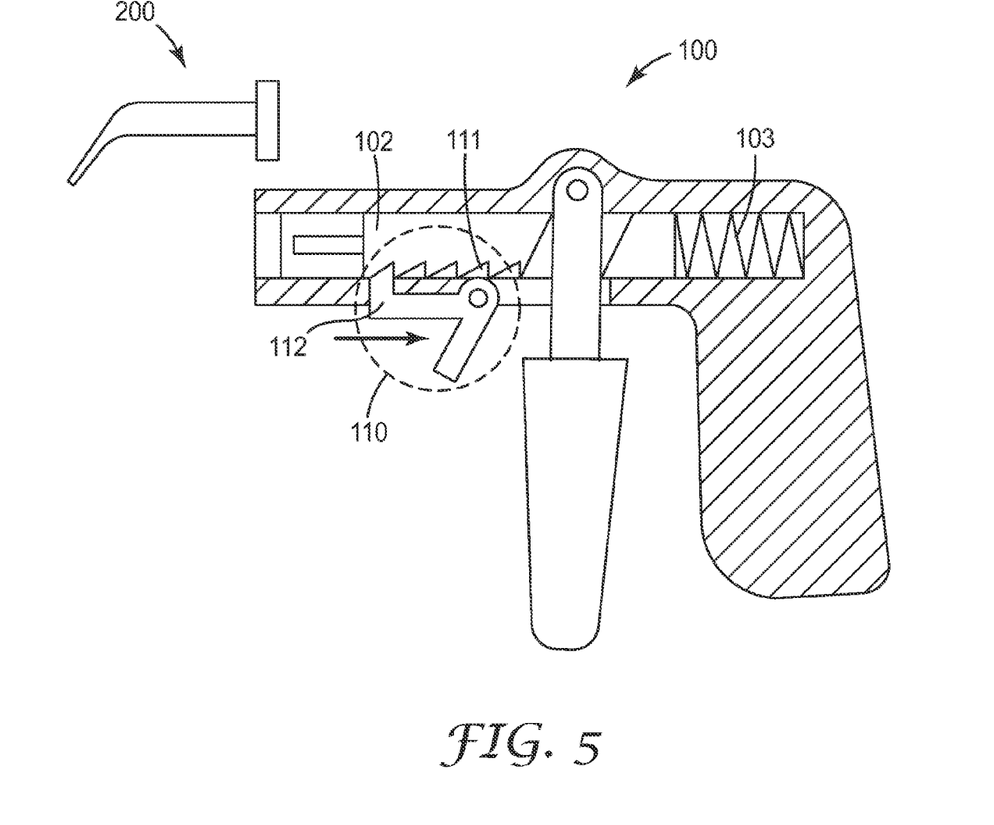
FIG. 5 shows the device of FIG. 4 in a loaded state.

FIG. 5 shows the dispensing device 100 with the piston 102 retracted and locked by the ratchet 112. The release mechanism 110 may be actuated as indicated by the arrow. Thereby the ratchet 112 may be disengaged from the teeth 111 in the plunger 102, and thereby the plunger 102 released to be advanced by the force of the spring 103. Another embodiment of the device 100 may not have a release mechanism, but an actuator for retracting a plunger against the force of the spring. The plunger of this embodiment may be retracted in a working stroke of the actuator, and released as the actuator is released. This may provide for a relatively inexpensive, but still conveniently usable device.

As described for FIGS. 1 to 3 also the dispensing device 100 may be used with a container 200 (indicated in FIG. 5) holding a dental composition. Features of embodiments as described in this specification may be used for other embodiments as appropriate.

The present invention has now been described with reference to several embodiments thereof. The skilled person will appreciate that many modifications can be made in the described embodiments without departing from the scope of the invention. Thus, the present invention is defined by the language of the claims.

The invention claimed is:

1. Device for dispensing a dental composition, comprising a plunger for extruding the dental composition from a container, an energy accumulator connectable to the plunger to advance the plunger at an extrusion force, an actuator which can be actuated for charging the energy accumulator, and a one-way clutch being movable by the actuator, wherein the device further comprises a force converter which allows the actuator to be actuated at an actuation force that is lower than the extrusion force available from the energy accumulator to advance the plunger; and wherein the one-way clutch is adapted to retract the plunger when moved in a first direction, but is movable relative to the plunger when moved in a second direction opposite the first direction.

2. The device of claim 1, wherein the actuator is adapted for manual actuation.

3. The device of claim 1, wherein the force converter converts a first motion of the actuator into a second motion for charging the energy accumulator at a force conversion ratio between the first and second motions that is selected from among approximately 3:1, 7:1, 8:1 and 10:1.

4. The device of claim 3, wherein the force converter converts a third motion transferred from the energy accumulator into a fourth motion for advancing the plunger at a force conversion ratio between the third and fourth motions that is selected from among approximately 3:1, 7:1, 8:1 and 10:1.

5. The device of claim 1, wherein the energy accumulator and the plunger cooperate such that energy from the energy accumulator is releasable for advancing the plunger, and retraction of the plunger causes the energy accumulator to be charged.

6. The device of claim 1, comprising a release mechanism which is adapted to prevent and release advancement of the plunger in a first and second mode of operation, respectively.

7. The device of claim 6, wherein the release mechanism allows retraction of the plunger in the first and second operation modes.

8. The device of claim 1, wherein the energy accumulator is a spring.

9. The device of claim 8, wherein the spring is one of a helical spring, and a spiral spring.

10. The device of claim 1, further comprising a container for the dental composition, wherein the container has a piston for extruding the dental composition from the container.

11. The device of claim 1, further comprising a dental composition wherein the dental composition is selected from among a dental restorative material, a dental retraction material, and a dental impression material.

12. A method of dispensing a dental composition, comprising the steps of:
    actuating an actuator of a dispensing device according to claim 1 at an actuation force; and
    extruding the dental composition independently from actuating the actuator at an extrusion force;
    wherein the actuation force is lower than about 75% of the extrusion force.

13. A kit of parts, comprising a device according to claim 1, and a plurality of springs having different spring characteristics.

14. Device for dispensing a dental composition, comprising a plunger for extruding the dental composition from a container, an energy accumulator connectable to the plunger to advance the plunger at an extrusion force, an actuator which can be actuated for charging the energy accumulator, and a one-way clutch being movable by the actuator, wherein the device further comprises a force converter which allows the actuator to be actuated at an actuation force that is lower than the extrusion force available from the energy accumulator to advance the plunger; wherein the force converter converts a first motion of the actuator into a second motion for charging the energy accumulator at a force conversion ratio between the first and second motions that is selected from among approximately 3:1, 7:1, 8:1 and 10:1; and wherein the force converter converts a third motion transferred from the energy accumulator into a fourth motion for advancing the plunger at a force conversion ratio between the third and fourth motions that is selected from among approximately 3:1, 7:1, 8:1 and 10:1.

* * * * *